US008419560B2

(12) United States Patent
Amini

(10) Patent No.: US 8,419,560 B2
(45) Date of Patent: Apr. 16, 2013

(54) SYSTEM AND METHOD FOR ADAPTIVE DELIVERY OF GAME BALLS BASED ON PLAYER-SPECIFIC PERFORMANCE DATA ANALYSIS

(76) Inventor: Alexander Andre Amini, Yorktown Heights, NY (US)

( * ) Notice: Subject to any disclaimer, the term of this patent is extended or adjusted under 35 U.S.C. 154(b) by 0 days.

(21) Appl. No.: 13/183,248

(22) Filed: Jul. 14, 2011

(65) Prior Publication Data

US 2013/0018493 A1 Jan. 17, 2013

(51) Int. Cl.
*A63B 69/36* (2006.01)
(52) U.S. Cl.
USPC .......................................... 473/212; 473/131
(58) Field of Classification Search ..................... 463/29; 273/192; 700/91; 473/212, 131
See application file for complete search history.

(56) References Cited

U.S. PATENT DOCUMENTS

| | | | | |
|---|---|---|---|---|
| 5,816,953 A | * | 10/1998 | Cleveland | 473/459 |
| 6,157,898 A | * | 12/2000 | Marinelli | 702/141 |
| 7,066,845 B2 | * | 6/2006 | Joseph | 473/431 |
| 2005/0209027 A1 | * | 9/2005 | Joseph | 473/431 |
| 2006/0276256 A1 | * | 12/2006 | Storek | 473/221 |
| 2007/0135225 A1 | * | 6/2007 | Nieminen et al. | 473/212 |
| 2007/0196800 A1 | * | 8/2007 | Douthit et al. | 434/252 |
| 2007/0298896 A1 | * | 12/2007 | Nusbaum et al. | 473/131 |
| 2011/0237344 A1 | * | 9/2011 | Nusbaum et al. | 473/278 |
| 2011/0294610 A1 | * | 12/2011 | Brenner et al. | 473/464 |

* cited by examiner

*Primary Examiner* — Masud Ahmed

(57) ABSTRACT

A game ball delivery apparatus that adjusts the delivery of game balls to the actual practice needs of the player returning the delivered game balls, based on a computer analysis of player performance data, including but not limited to data collected from inertial and physiological sensors. The parameters of delivery, such as trajectory, speed, and interval of successive balls, are modified in real-time, as the player is training. One or more highly miniaturized sensors for collecting performance data are worn by the player without affecting the player's motions. A computer capable of analyzing said sensor data, selects delivery parameters for subsequently delivered balls, and transmits said delivery parameters to the ball ejector controller. Further, the system may optionally include a means for generating a feedback signal to the player to indicate deviations of the measured motion of the player from reference performances of the motion.

10 Claims, 15 Drawing Sheets

| Description | Symbol |
|---|---|
| Start timecode of Stroke | $S_s$ |
| End timecode of Stroke | $E_s$ |
| Time period when magnitude is greater than 2 | FS |
| Time | $t$ |
| Start timecode of Full Stroke | $S_{FS}$ |
| End timecode of Full Stroke | $E_{FS}$ |
| Number of samples from the start to the end of a stroke | $n$ |
| Number of samples from the start to the end of a full stroke | $N$ |
| Contact Point | CP |
| Timecode of Contact Point | $CP_t$ |
| Accelerometer X at timecode | $A_x(t)$ |
| Accelerometer Y at timecode | $A_y(t)$ |
| Accelerometer Z at timecode | $A_z(t)$ |
| Gyroscope X at timecode | $G_x(t)$ |
| Gyroscope Y at timecode | $G_y(t)$ |
| Gyroscope Z at timecode | $G_z(t)$ |
| Magnetometer X at timecode | $H_x(t)$ |
| Magnetometer Y at timecode | $H_y(t)$ |
| Magnetometer Z at timecode | $H_z(t)$ |
| Timecode of Max Magnitude Occurrence | $MM_t$ |

Fig. 11

| Description | Formulas |
|---|---|
| Magnitude of Acceleration at Timecode | $Mag(t) = \sqrt{(A_x(t))^2 + (A_y(t))^2 + (A_z(t))^2}$ |
| Roll at Timecode (Radians) | $\varphi(t) = \arctg\left(\dfrac{A_y(t)}{A_z(t)}\right)$ |
| Pitch at Timecode (Radians) | $\theta(t) = \arctg\left(\dfrac{A_x(t)}{\sqrt{(A_y(t))^2 + (A_z(t))^2}}\right)$ |
| Yaw at Timecode (Radians) | $\Psi(t) = \arctg\left(\dfrac{((H_y(t)) \cdot \cos\varphi) - ((H_z(t)) \cdot \sin\varphi)}{((H_x(t)) \cdot \cos\theta) + ((H_y(t)) \cdot \sin\varphi) + ((H_z(t)) \cdot \sin\theta \cdot \cos\varphi)}\right)$ |

| Description | Formula |
|---|---|
| Minimum Acceleration X across a stroke | $\min\{A_x(t) \mid t \in [S,E]\}$ |
| Minimum Acceleration Y across a stroke | $\min\{A_y(t) \mid t \in [S,E]\}$ |
| Minimum Acceleration Z across a stroke | $\min\{A_z(t) \mid t \in [S,E]\}$ |
| Maximum Acceleration X across a stroke | $\max\{A_x(t) \mid t \in [S,E]\}$ |
| Maximum Acceleration Y across a stroke | $\max\{A_y(t) \mid t \in [S,E]\}$ |
| Maximum Acceleration Z across a stroke | $\max\{A_z(t) \mid t \in [S,E]\}$ |
| Average Acceleration X across a stroke | $\sum_{t=S_s}^{E_s} \frac{A_x(t)}{n}$ |
| Average Acceleration Y across a stroke | $\sum_{t=S_s}^{E_s} \frac{A_y(t)}{n}$ |
| Average Acceleration Z across a stroke | $\sum_{t=S_s}^{E_s} \frac{A_z(t)}{n}$ |

| Description | Formula |
|---|---|
| Average Acceleration X across a Full Stroke | $\sum_{t=S_{FS}}^{E_{FS}} \frac{A_x(t)}{N}$ |
| Average Acceleration Y across a Full Stroke | $\sum_{t=S_{FS}}^{E_{FS}} \frac{A_y(t)}{N}$ |
| Average Acceleration Z across a Full Stroke | $\sum_{t=S_{FS}}^{E_{FS}} \frac{A_z(t)}{N}$ |
| Maximum Magnitude Across a Stroke | $MM = \max\{Mag(t) \mid t \in [S,E]\}$ |
| Roll at Max Magnitude Timecode | $\varphi(MM_t)$ |
| Pitch at Max Magnitude Timecode | $\theta(MM_t)$ |
| Yaw at Max Magnitude Timecode | $\psi(MM_t)$ |

| Stroke Type | Rule | Motion Adjustment Feedback |
|---|---|---|
| All | If $\sqrt{(A_x(CP_t))^2 + (A_y(CP_t))^2 + (A_z(CP_t))^2}$ and/or $A_z(CP_t)$ of stroke is <= 80% of same value for model stroke | Drive Through the Ball More |
| All | If $A_x(CP_t)$ of stroke is <= 80% of same value for model stroke | More upward acceleration |
| All | If $\sqrt{(A_x(CP_t))^2 + (A_y(CP_t))^2 + (A_z(CP_t))^2}$ and/or $max\{Mag(t)\|t \in [S, E]\}$ of stroke is <= 80% of same value for model stroke | Hit Harder |
| Forehands and backhands | If $\varphi(CP_t)$ of the dominant arm WIMUs of stroke are <= 80% of same value for model stroke | Raise the face of racquet on contact |
| Serves and overheads | If $\theta(CP_t)$ of the dominant arm and wrist WIMUs of stroke are <=80% OR >=120% of same values for model stroke | Keep arm straighter at contact point |
| Kick serves | If $\Psi(CP_t)$ of the dominant arm and wrist WIMUs of stroke are <=90% OR >=120% of same value for model stroke | Toss ball slightly farther to the less dominant side |
| Forehands and backhands | If $\sum_{t=S_s}^{E_s} G_y(t)$ of stroke is <= 80% of same value for model stroke | Greater shoulder turn |
| Slices and dropshots | If $min\{A_x(t)\|t \in [S, E]\}$ of the dominant arm WIMU of stroke are >=120% of same value for model stroke | More downward acceleration |

Fig. 14

SYSTEM AND METHOD FOR ADAPTIVE DELIVERY OF GAME BALLS BASED ON PLAYER-SPECIFIC PERFORMANCE DATA ANALYSIS

TECHNICAL FIELD

The present invention relates to the field of motion sensing devices for enhanced training of physical skills, and more particularly to the intelligent control of game ball delivery based on the analysis of player performance data.

BACKGROUND ART

Game ball delivery apparatus are a common means for enhanced practice and instruction of sports such as tennis, baseball, soccer, and table tennis. The game ball delivery apparatus sequentially ejects game balls such that a player can practice by returning the balls as if playing with an opponent or instructor. To enable the player to practice a variety of strokes, the game ball delivery apparatus may allow the user to select from options that control the trajectories of the game balls, such as the direction, speed, and interval between successive balls. The game ball delivery apparatus may allow the user to set such options for each ball or to select from a set of programs pre-defined by the manufacturer of the apparatus. For example, a tennis ball delivery apparatus may provide a program that challenges the player to alternate between forehand strokes and backhand strokes. U.S. Pat. No. 4,269,163 details a game ball delivery apparatus that allows a user to select from such pre-defined options and programs.

Providing such pre-defined options and programs allows the user to select the program that the user considers most desirable for their current practice needs. However, the apparatus is limited to the pre-defined options established by the manufacturer, and those pre-defined options may not reflect the actual needs of the player. Additionally players using such machines are required to determine which pre-defined options would be most beneficial to improving their skill. It would be desirable to have a game ball delivery apparatus that could sense the player's performance ability, and adapt the delivery of game balls according to the actual practice needs of that specific player.

U.S. Pat. No. 4,915,384 describes a player adaptive sports training system that includes a target for which the player should aim when returning a delivered ball. The system described by U.S. Pat. No. 4,915,384 is capable of detecting whether the player hits said target with returned ball and of adjusting parameters, such as delivered ball speed or target to meet the skill level of that player. Thus, U.S. Pat. No. 4,915,384 adapts game ball delivery to current ability of the player to hit a target, as opposed to identifying the player's weaknesses and adapting the program to eliminate those weaknesses. Also, U.S. Pat. No. 4,915,384 is limited by sensing only if a target is hit and not sensing the player's actual motions, and thus not detecting whether the player is using proper movements and orientations. For example, in the game of baseball, hitting a ball such that it is easily caught before touching the ground (commonly referred to as a pop fly) is undesirable even if it does reach a target. It would be desirable to have the game ball delivery apparatus sense the player's orientation and movements, to detect conditions under which the player is not performing optimally, and to adjust the game ball delivery program to concentrate the player's practice program on eliminating weaknesses and refining their technique.

U.S. Pat. No. 5,816,953 describes an interactive apparatus that senses where the player's returned ball lands such that it can display the returned position on a video screen, but also does not adapt the delivery of balls based on this information.

Therefore, there exists a need for an apparatus capable of adapting game ball delivery based on player-specific performance data, such as the player's orientation and movements.

SUMMARY OF INVENTION

The present invention addresses the need to have a game ball delivery apparatus that adjusts the delivery of game balls to the actual practice needs of the player returning the delivered game balls.

The present invention is a game ball delivery apparatus in which the means for ejecting game balls is program controlled and capable of receiving data signals to set the parameters of said ball delivery based on a computer analysis of player performance data, including but not limited to inertial and physiological measurements of the player collected from one or more sensors.

In a preferred embodiment, the present invention includes a means for successively ejecting a plurality of game balls, where the parameters of delivery, such as trajectory, speed, and interval of successive balls, is program controlled and the parameters of said program may be modified by sending data signals to said controller; one or more highly miniaturized sensors that can be attached to the player or sports equipment without affecting the player's motions, where the sensors capture performance data from the player and communicate said digital sensor data to a computer for analysis; and a computer capable of analyzing said digital sensor data, selecting delivery parameters for subsequently delivered balls, and transmitting said delivery parameters to the program controlling the game ball delivery. The preferred embodiment includes a Measured Play mode, in which game ball delivery is adapted according to player performance data; and a calibration mode, in which a player creates optimum, player-specific reference profiles, which are stored in the computer. In calibration mode, game balls are delivered at a level that enables the player to perform the correct orientations and movements for a plurality of stroke types, so that reference profiles may be captured, stored, and used during Measured Play mode to detect deviations from the correct movements and orientations.

Another preferred embodiment of the present invention includes the computer also generating feedback to indicate deviations of the measured motion of the player from a reference motion representing the desired orientations and movements of a player correctly performing the intended game ball return. The feedback is sent as an indicator signal to the player, where the indicator signals include but are not limited to: audible; visual; or physical, such as a pattern of vibrations.

In yet another preferred embodiment of the present invention, the computer program also stores stroke selection, accuracy data, and feedback data throughout the training session such that a report comprising a summary of performance throughout the complete training session may be generated for retrospective analysis of the training session. In this alternate preferred embodiment, the user may select from a plurality of summary and detail report components. The addition of the retrospective analysis report is to allow the user and/or their coach to review the performance over the full training session and components of the training session, and to compare performance over multiple training sessions.

An advantageous effect of the present invention is that by adapting the program of play based on player performance sensors, the game ball delivery apparatus creates a program customized to the practice needs of the player, instead of being limited to options and programs defined by the manufacturer.

Another advantageous effect is that the program can be adapted based on the player's performance without manual interventions of the user, instead of requiring the user adjust the options and programs manually or by remote control.

Another advantageous effect is that the program can address the measured and actual technical weaknesses of the player, such as deviations of the measured movements and orientations of the player from a reference profile of movements and orientations of a player correctly performing the intended ball return, instead of the needs perceived by the player or coach.

Another advantageous effect is that the program can process data from physiological sensors and adapt game ball delivery to physiological targets such as heart rate.

Another advantageous effect is that the program automatically determines the appropriate options and program for game ball delivery, instead of requiring the user determine how to translate their practice needs into a set of options and programs for the apparatus.

Another advantageous effect is that the apparatus also generates an indicator signal as feedback to the player in addition to adjusting the game ball delivery options and program, so that the player can adjust their movements and orientation as they continue to return delivered balls.

Yet another advantageous effect is a player can use calibration mode to capture player-specific reference profiles. As the player's abilities improve, the player may chose to re-enter calibration mode to capture improved reference profiles. A player may choose to use their own reference profiles, or those of a more skilled player.

More advantageous effects of the present invention will become obvious from the drawings and ensuing descriptions.

BRIEF DESCRIPTION OF DRAWINGS

FIG. 11 and FIG. 12 detail key definitions of variables used to calculate the features in FIG. 13.

FIG. 13 details how each of the feature values that make up the profile for a single sample stroke are computed.

FIG. 14 provides example rules and resulting motion adjustment feedback for tennis training.

DESCRIPTION OF EMBODIMENTS

Figure 1:
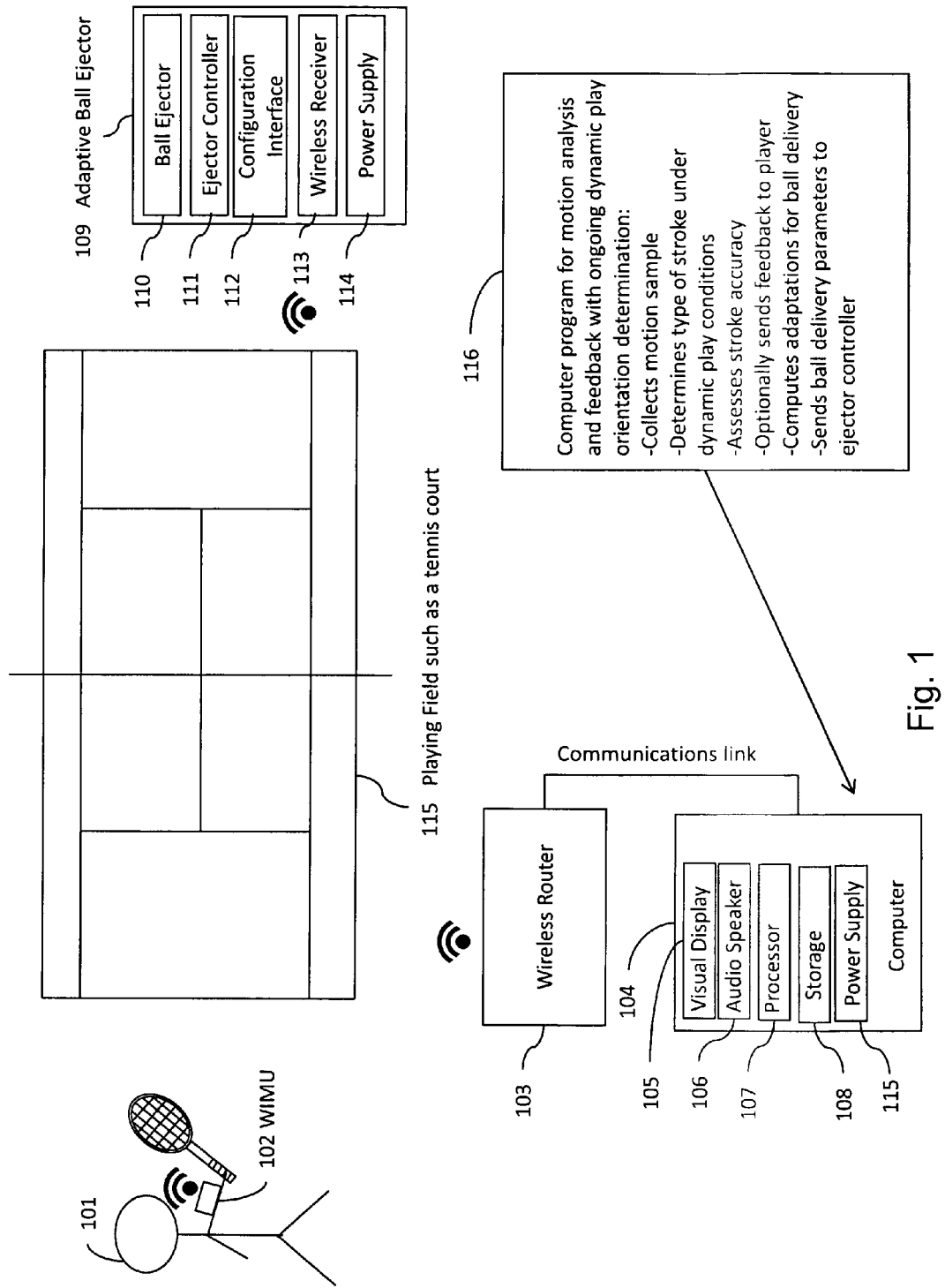
FIG. 1 depicts users utilizing the configuration in which the adaptive ball ejector communicates wirelessly to a computer that analyzes motion sensor data and provides program adaptations to the adaptive ball delivery controller.

FIG. 1 shows an adaptive tennis ball ejector as an example of the preferred embodiment of the present invention. The adaptive tennis ball ejector (109) is positioned opposite the user (101) on the tennis court (115) so that the balls can be delivered to the user similarly to how an opposing player would. In this example, the user (101) is wearing a WIMU (102) on their dominant playing arm. The WIMU (102), or Wireless Inertial Measurement Unit, is an example of a motion sensor. The WIMU (102) captures movement and orientation data from the user and transmits the data wirelessly to the computer (104) via the wireless router (103). Those skilled in the art will understand that the wireless router (103) may alternatively be a wireless base station, or other device capable of sending and receiving wireless transmissions. The computer (104) includes a processor (107), which executes a computer program (116) that analyzes the movement and orientation data from the user in order to assess the user's performance and to generate parameters for adaptive ball delivery. The computer (104) transmits the parameters to the adaptive ball ejector (109) via the wireless router. The wireless receiver (113) received the transmitted parameters and sends to the ejector controller (111). The ejector controller (111) receives the updated parameters and integrates the updated parameters into its local state, including trajectory, speed, and interval of successive balls. The ejector controller (111) includes a timer based on the interval of successive balls parameter. When the timer fires, the ejector controller signals the ball ejector (110) to deliver the next ball using the updated trajectory and speed parameters. The computer (104) and the adaptive ball ejector (109) each include power supplies, which are labeled 115 and 114, respectively. The adaptive ball ejector (109) optionally includes a configuration interface (112) so the user may enter configuration information locally. Configuration information may also be entered via the visual display (105) of the computer (104). Feedback to the user is optionally transmitted by the visual display (105) or audio speaker (106). The computer storage (108) is used to store reference motion profiles to enable user motion assessment and to track ongoing user performance.

Figure 2:
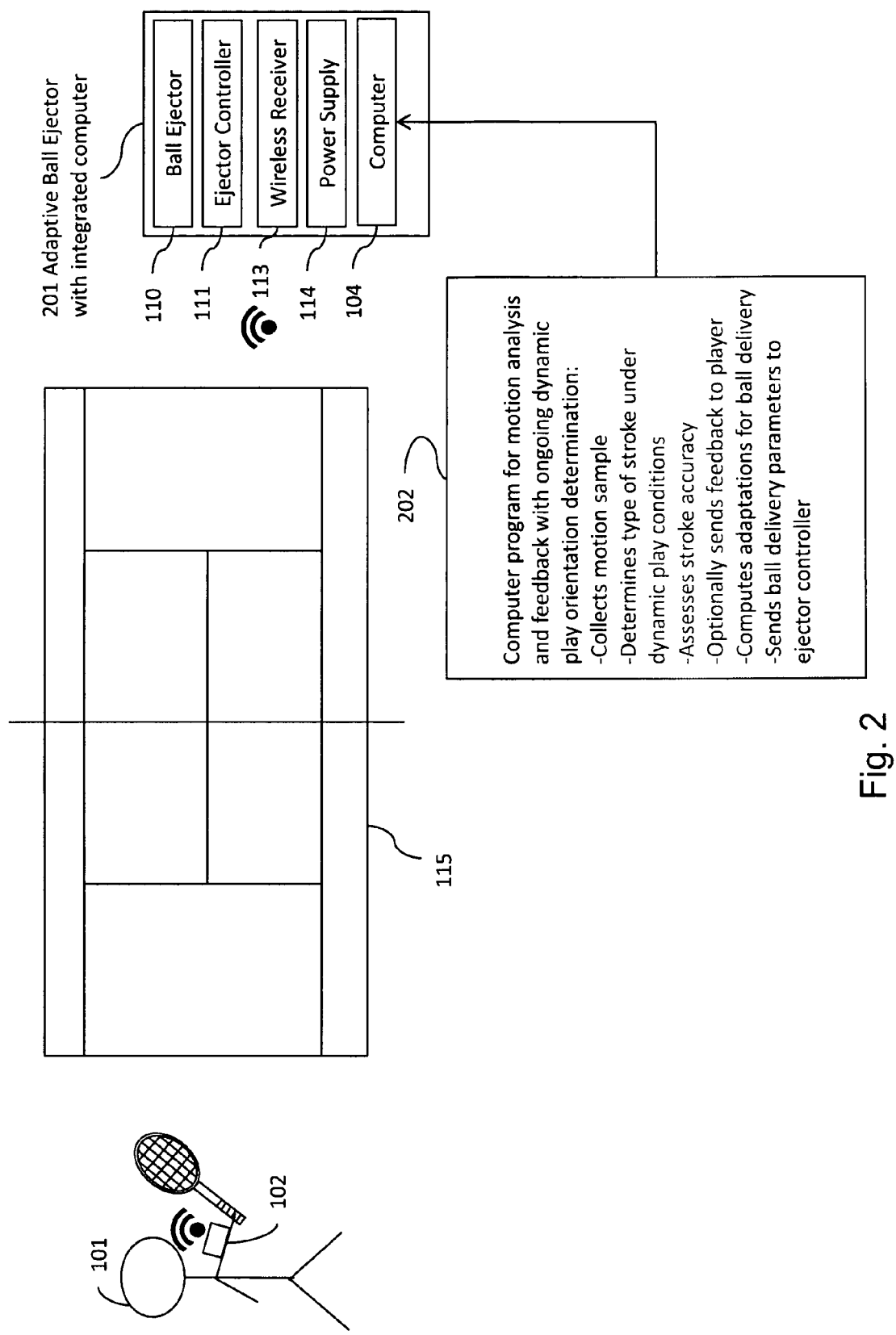
FIG. 2 depicts users utilizing the configuration in which the computer that analyzes motion sensor data is integrated into the adaptive ball ejector.

FIG. 2 illustrates an adaptive tennis ball ejector integrated with a computer as another example of the preferred embodiment of the present invention. In FIG. 2, the adaptive ball ejector (201) and player are positioned at opposite ends of the tennis court as described for FIG. 1. In FIG. 2, the computer is integrated into the adaptive ball ejector (109). In this configuration, digital sensor data transmitted by the motion sensors (102) is received by the wireless receiver (113) and communicated to the computer (104) for analysis. The computer (104) directly communicates parameter updates to the ejector controller (111).

Figure 3:
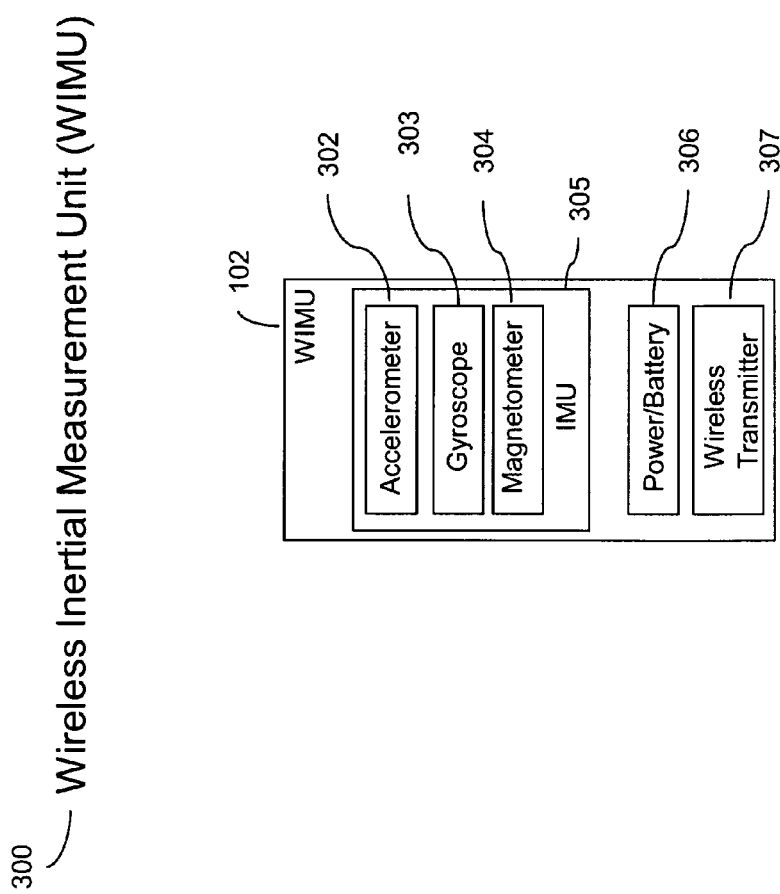
FIG. 3 depicts a single WIMU sensor configuration with integrated IMU.

FIG. 3 depicts the components of an example WIMU (102). In this example, the WIMU includes an accelerometer (302), which is a sensor to detect changes in acceleration (changes in velocity) along the X, Y, or Z axis. The WIMU also includes a gyroscope (303), which is a sensor to detect orientation in 3 dimensions, and tri-axis magnetometer (304), which measures the strength and direction of the earth's magnetic field and can be fused with accelerometer and gyroscope data to help compensate for drift. The accelerometer, gyroscope, and magnetometer together are referred to as the Inertial Measurement Unit (IMU) (305). The WIMU also includes a power supply (i.e., battery) (306) and a wireless transmitter (307). The WIMU samples readings from the gyroscope, magnetometer, accelerometer, and wirelessly transmits those readings, along with the timecode at which the sample reading was taken. All of the inertial readings are captured in analog and converted to digital signals for transmission.

Figure 9:
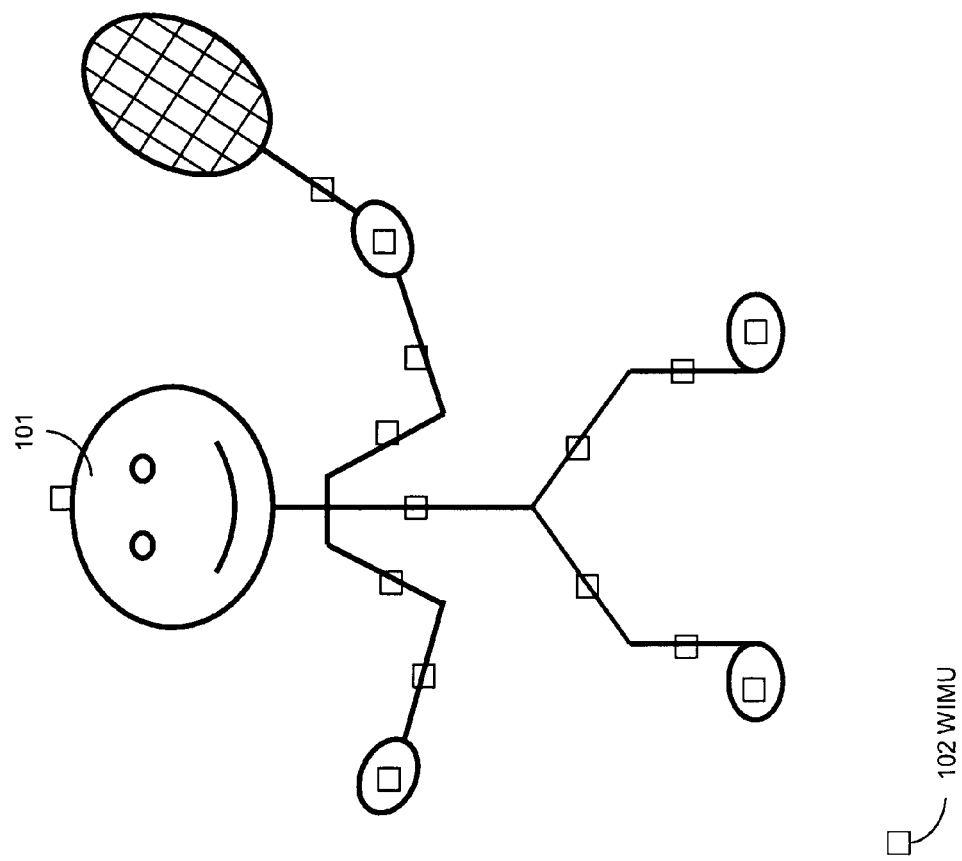
FIG. 9 illustrates placement of additional sensors that may optionally be used in the present invention.

FIG. 9 illustrates how a plurality of WIMU (102) may be positioned to capture movement and orientation data from the user (101). Those skilled in the art will recognize that different subsets of the sensors displayed in FIG. 9 may be chosen according to a variety of reasons, including the motion being assessed, user comfort, and expense. FIG. 9 also illustrates the WIMU may be placed on the sports instrument, including tennis rackets, golf clubs, and hockey sticks.

Figure 4:
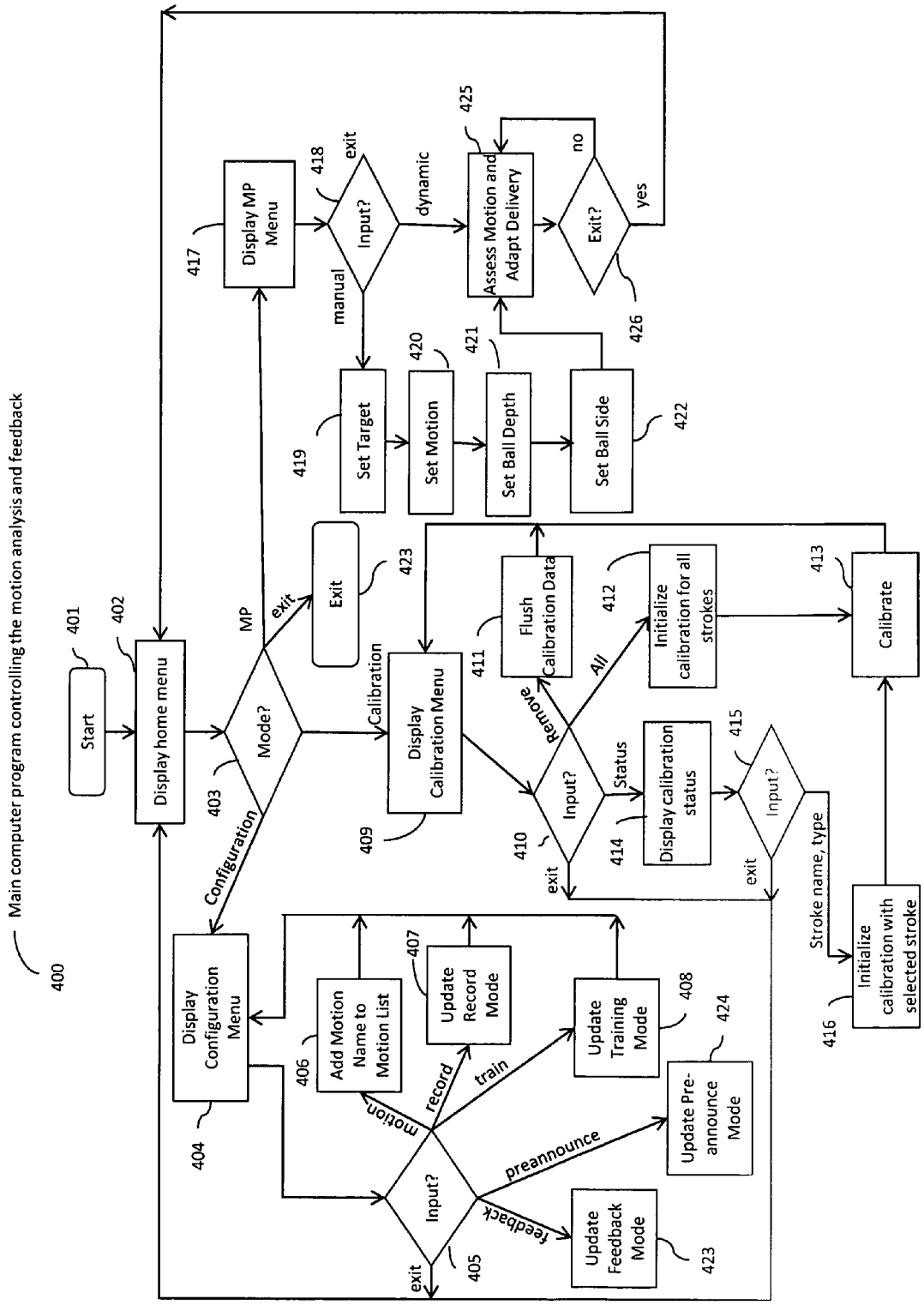
FIG. 4 is a flow chart of the computer program that controls the motion analysis and adaptive ball delivery.
Figure 8:
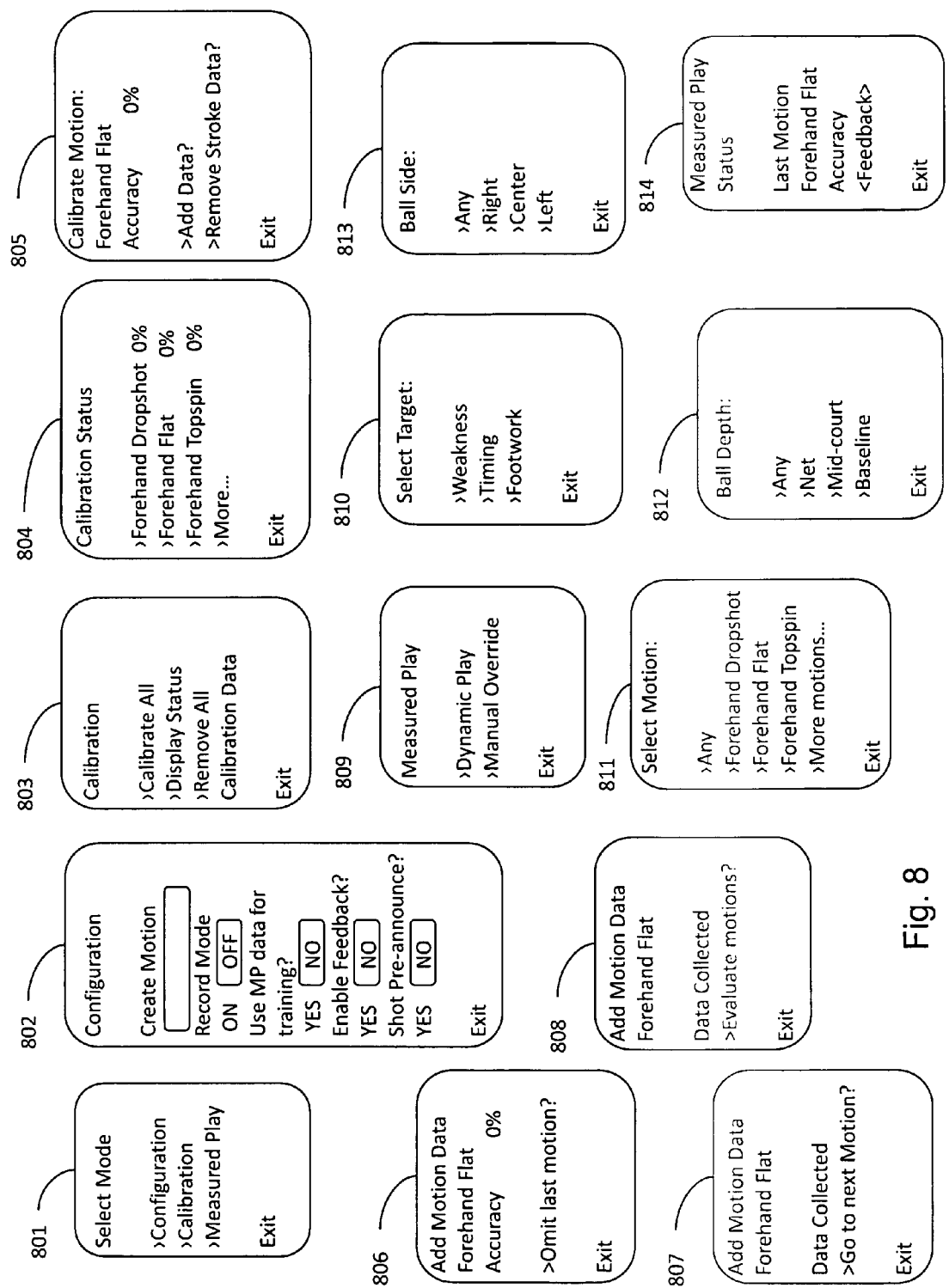
FIG. 8 provides the menus displayed by the computer program that controls the motion analysis and feedback.

FIG. 4 is a flow chart of the main computer program that controls the motion analysis and adaptive ball delivery, and is generally designated 400. The menus to be displayed by the computer program (400) on the visual display (105) are provided in FIG. 8. The first action taken by the program after start (401) is to Display the home menu (402). The home menu (801) prompts the user to select from Configuration mode, Calibration mode or Measured Play (MP) mode, or to Exit. If Exit is selected, the program exits (423). Once the user responds by selecting a mode, the mode requested is evaluated (403) and the appropriate mode entered.

If Configuration mode is selected, the program will enter Display Configuration Menu (404). The displayed Configuration Menu (802) allows the user to create a new motion, alter Record Mode, alter Use MP data for training, alter Pre-announce Mode, alter Feedback Mode, or Exit. Once the user enters their input, the program will evaluate that input (405). If a new motion name is entered, the program will Add Motion Name to the Motion List (406) by first checking that the name is not already in use and if not, by creating an entry in the Reference Motion database (DB). The Reference Motion DB and its entries will be detailed in the discussion of FIG. 5. If the setting for Record Mode is altered, the program will update the record mode (407). When Record Mode is ON, the profiles captured in Measured Play and their feedback will be stored in a circular buffer. When Record Mode is OFF, the profiles captured during Measured Play are deleted after feedback is provided to the user. If the setting for Use MP data for training is altered, the program updates the training mode (408). When Use MP data for training is YES, motion profiles captured during Measured Play will be added to the Reference Motion DB. If Use MP data for training is NO, only motion profiles captured during Calibration are added to the Reference Motion DB. Adding profiles from Measured Play has the advantage of allowing the user to easily build a more comprehensive Reference Motion DB. Not adding profiles from Measured Play has the advantage of allowing the user to screen the profiles used for reference through Calibration mode. If the setting for Enable Feedback is altered, the program will Update Feedback Mode (423). When feedback is enabled, the system will provide feedback on performance to the user. When feedback is not enabled, the system will adapt ball delivery but not transmit feedback indicators to the user. If Pre-announce Shot is altered, the program will enter Update Pre-announce Mode (424). When Pre-announce Shot is enabled, the system will transmit the expected motion to the user via the audio speaker. Enabling pre-announce shot has the advantage of enabling the system to more closely control the training program by specifying which shot the user should attempt, instead of allowing user shot selection. When Pre-announce shot is not enabled, the user is not provided with input on which shot to attempt.

If Calibration mode is selected, the program enters calibration mode and displays the Calibration menu (409) as illustrated in 803. After the menu is displayed, program awaits input (410). If the user selects "Remove All Calibration Data" from 803, the program will remove the calibration data for all strokes (411) and return to Display Calibration Menu (409). If the user selects "Calibrate All," the program will update state to reflect that additional reference data for all strokes should be collected (412), and then will enter Calibrate (413). The detailed flow for the Calibrate (413) procedure is provided in the description for FIG. 5. If the user selects "Display Status" (414) the program will display calibration status for all strokes (804) and allow the user to select a specific stroke (415). If the user selects a specific stroke, detailed calibration status will be displayed (805) and the user will be allowed to chose between adding additional calibration data for that specific stroke or starting a fresh set of reference data for that stroke by first removing existing stroke data. Once the user selects the stroke and whether new calibration data should be added to the existing reference DB or the existing data should be removed, that input is sent to Initialize calibration with selected stroke (416), which updates program state by removing existing reference data (if requested) and setting the stroke name. The program then enters Calibrate (413). The detailed flow for the Calibrate (413) procedure is provided in the description for FIG. 5. Once Calibrate (413) is complete, the program returns to Display Calibration Menu (409) in case additional calibration is desired. The user may chose to exit Calibration mode from either Display Calibration Menu (409) via 410 or Display Calibration Status (414) via 415.

If Measured Play is selected from the menu in 801, the program enters Display MP Menu (417) in which the program displays the Measured Play menu (809), and awaits input (418). From 809, the user may chose to enter Dynamic Play mode or to manually specify motion and placement information. If dynamic play mode is selected, Assess Motion and Adapt Delivery (425). If manual override is specified, then Set Target (419) is entered and Select Target menu (810) is displayed. The Select Target menu (810) illustrates example target options of Weakness, Timing, and Footwork. The Weakness target option will adapt ball delivery to exercise those shots, court positions, and timings at which the user most requires practice. The Timing target option will adapt ball delivery primarily to exercise those timings (shot speed and ball delivery interval) at which the user most requires practice. The Footwork target option will adapt ball delivery to exercise those shot sequences in which the player most requires practice. A detailed explanation of how these parameters map to ball delivery parameters transmitted to the ejector controller (111) is provided with FIG. 15.

After Set Target (419) completes, Set Motion (420) allows the user to limit the ball delivery to specific types of motions (e.g., Forehand Flats only), or to allow "Any" motions to be targeted (811). Set Ball Depth (421) allows the user to limit the court depth at which the ball is delivered, or to allow the system to select from any court depths (812). Set Ball Side (422) allows the user to limit the court side to which the ball is delivered, or to allow the system to select from any court side (813). After manual configuration is complete, the system enters Measured Play mode via Assess Motion and Adapt Delivery (425). A detailed explanation of the Assess Motion and Adapt Delivery (425) procedure is provided with FIG. 6. If the user exits from the Assess Motion and Adapt Delivery state via 426, they will be returned to the home menu (402).

Figure 5:
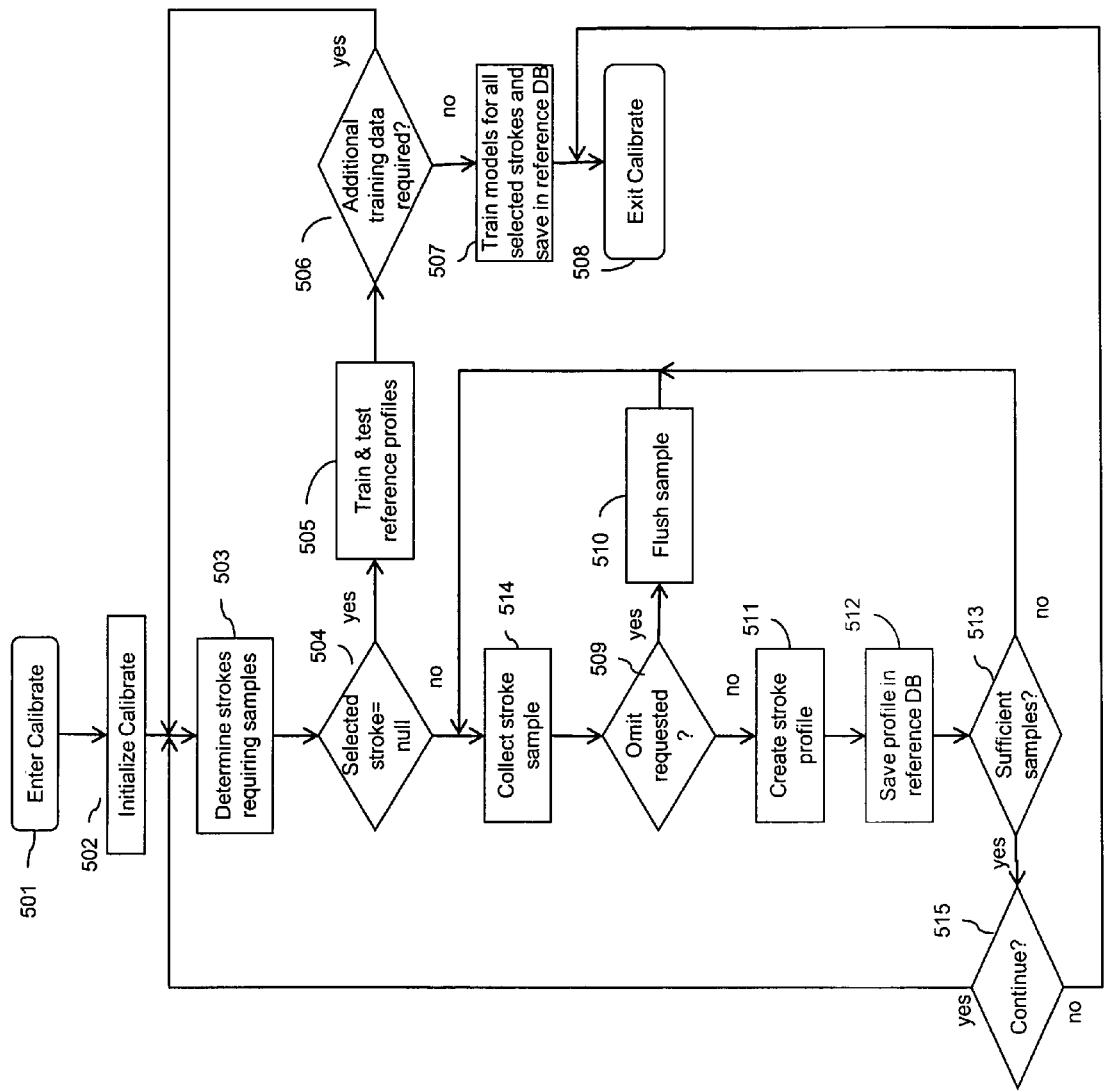
FIG. 5 details the flow chart for the Calibration portion of the computer program that controls the motion analysis and adaptive ball delivery.

FIG. 5 details the flow chart for the Calibrate procedure (413) of the computer program (detailed in FIG. 4) that controls the motion analysis and feedback. The objective of Calibrate is to capture sufficient data such that when the user enters Measured Play mode, the program can: 1) determine with high accuracy whether measured motions are of a given shot type, 2) assess deviations from the measured motions of correct performances of that shot type, and 3) provide feedback so the user can improve motion. Assessing a given shot type and deviations requires sufficient performance data of the shot type under consideration, as well as performance data from incorrect performances, including other shot types and incorrect performances. FIG. 5 illustrates how the program in this invention collects this performance data and assesses whether it has sufficient performance data to enable high accuracy assessments during Measured Play.

The program enters Calibrate at 501, and Initializes Calibrate (502) by setting internal state to the user specified strokes to be calibrated and by creating temporary buffer space to hold incoming sensor data to be evaluated. The program will then Determine strokes requiring samples (503) by checking which of the strokes to be calibrated have sufficient samples in the reference database to train and test models for that stroke and which require additional samples. If additional samples are required, the program will Collect stroke samples (514), which is explained in detail in FIG. 7. While the program is collecting samples, it displays a menu (806) that shows the current calibration status and allows the user to choose to omit the most recently collected sample. If the user requests to omit the most recently selected sample (509), the sample will be flushed (510). If the sample is not omitted, a stroke profile is created (511). The stroke profile is a summarization of important features of the stroke that can be used to train a model representing the stroke and to assess deviations from the model. The stroke profile is described with FIG. 13.

The profile created in 511 is stored in the reference database (512) so that it can later be used to train and test models in 505, and then the program tests whether sufficient samples have been collected (513) to support the train and test process in 505. The number of samples sufficient for train and test is dependent on the train and test method, which is described for FIG. 10. If sufficient samples have been collected the screen is updated to allow the user to go to the next motion (807) if additional motions require calibration, or to evaluate motions (808) if no addition motions require calibration. The user may also choose to exit calibration mode from 807 or 808. Depending on the user's choice from the menus 807 or 808, the program will Continue (515) by returning to Determine strokes requiring samples (503) or exit calibrate (508).

When Determine strokes requiring samples (503) determines additional samples are not required, the selected stroke will equal null (504) and then the program will Train and test reference profiles (505). The preferred embodiment for Train and test reference profiles (505) is explained in detail in FIG. 10. The results of Train and test reference profiles (505) are assessed to determine if Additional training data is required (506) to attain the accuracy required for Measured Play, and if not, models are trained for all selected strokes and saved in reference DB (507), and then Calibration mode is exited (508). If Additional data is required (506), the program returns to collect more data in Determine strokes requiring data (503).

Figure 7:
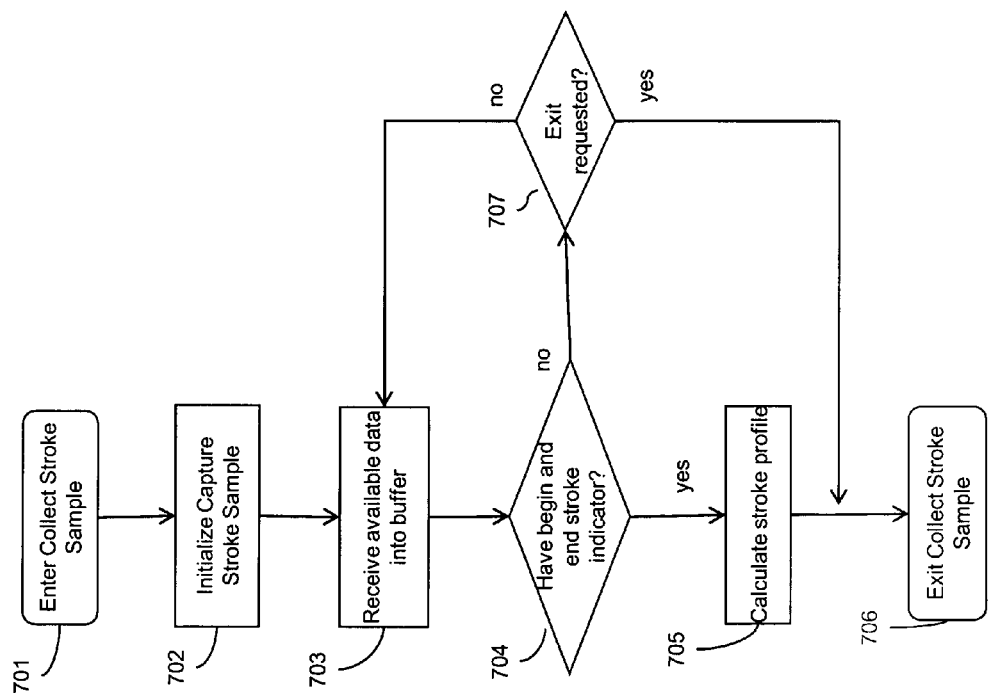
FIG. 7 details the flow chart for the Collect Stroke Sample portion of the computer program that controls the motion analysis and adaptive ball delivery.

FIG. 7 details the procedure for collecting a stroke sample. The procedure is entered at 701, and then proceeds to Initialize Capture Stroke Sample (702), which clears capture buffers and internal capture state. The program will continue to Receive available data into buffer (703) by reading data from the WIMU sensors into its internal buffers until a begin and end stroke indicator is detected. The preferred embodiment of the present invention tests for a begin stroke indicator and an end stroke indicator (704) by testing the magnitude of the accelerometer sensor from the WIMU positioned on the dominant arm of the player. Those skilled in the art will understand that additional sensor data and techniques may be used in computing a begin stroke indicator and end stroke indicator. If the wait for begin and end stroke indicators (704) is interrupted before the indicators are received, the program checks whether the user requested program exit (707) from the Measured Play status menu (814). If Exit is requested (707), the program moves to Exit (706), otherwise it returns to receive additional data (703). Once the begin and end stroke indicators are received, the program Calculates the stroke profile (705).

The stroke profile is computed from the WIMU sensor data collected during the performance of the stroke. FIG. 13 provides the features used to compute the stroke profile stored in the reference database in the preferred embodiment of the present invention. FIG. 11 and FIG. 12 provide definitions of variables used to calculate the features in FIG. 13. These features are specific to measured motions and orientations for tennis strokes, however those skilled in the art will understand that similar features specific to other sports, such as golf and hockey, can be used in this invention. In addition to the features computed for each stroke, each stroke profile includes the actual stroke type that was being performed. We refer to this actual stroke type as the ground-truth stroke type. Once the stroke profile is calculated, the Collect Stroke Sample procedure is exited (706).

Figure 10:
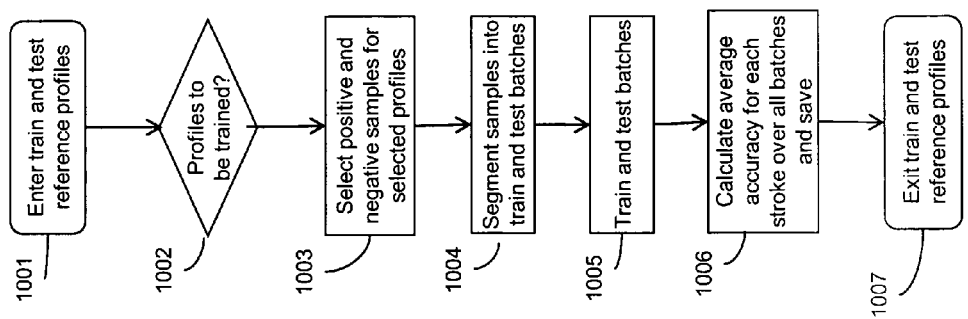
FIG. 10 details the flow chart for the train and test reference profiles portion of the program that controls the motion analysis and adaptive ball delivery.

FIG. 10 details the Train and test reference profiles procedure, which begins with Enter train and test reference profiles (1001). The program accesses the reference database to determine which of the strokes selected for calibration have sufficient reference profiles in the reference database (1002). The number of profiles required to train and test is dependent on the type of model to be trained.

The preferred embodiment of this invention uses a data mining technique called Support Vector Machines (SVM) to train and test a model for each stroke type. Additional information on SVM can be found in "An Introduction to Support Vector Machines and Other Kernel-based Learning Methods," by Cristianini, et al [Cristianini]. Those skilled in the art will understand that other classification techniques, such as decision trees, and K-Nearest Neighbor (KNN) could be used to train and test models for the present invention. Additional information on decision tree and K-NN classifiers can be found in "A survey of decision tree classifier methodology," by Safavian and Landgrebe [Safavian]; and "Nearest-Neighbor Methods in Learning and Vision," by Shakhnarovish and Indyk [Shakhnavovish], respectively. In the following two paragraphs, we describe how a classification technique, such as SVM, can be used to calibrate models and assess performance against those models.

In training mode, SVM accepts samples that are labeled as positive and negative examples of the model to be trained. For example, if a model of the Forehand Flat stroke is being trained, then profiles for which the ground-truth stroke type is Forehand Flat would be labeled as positive samples and profiles of all other strokes would be labeled as negative samples. In the preferred embodiment of the present invention, the stroke profile, which is a list of feature values computed from the WIMU sensor data, is the sample provided to SVM. FIG. 13 details how each of the feature values that make up the profile for a single sample stroke are computed.

In test mode, SVM accepts samples for which the same features have been calculated and uses the trained model to classify the samples as positive or negative examples of the modeled stroke. The accuracy of the model is determined by comparing the positive or negative classification of each stroke profile to the ground-truth stroke type of the same stroke profile.

Once the procedure in FIG. 10 determines there are profiles available for training (1002), it selects the set of positive and negative samples for selected profiles (1003) from the reference database to be used for training a model for each stroke type. For each model to be trained, it Segments samples into test and train batches (1004). The present invention randomly selects 80% of the samples in each batch for training the model and then uses the remaining 20% for testing that model. Those skilled in the art will understand that other techniques for segmenting samples into batches may be used with the present invention. The program in FIG. 10 then uses SVM train mode to train a model and SVM test to test that model (1005). The average accuracy is computed for each model across all batches, and this accuracy value is stored in the reference DB with the model (1006). Finally, the train and test reference profiles procedure is exited (1007).

Figure 6:
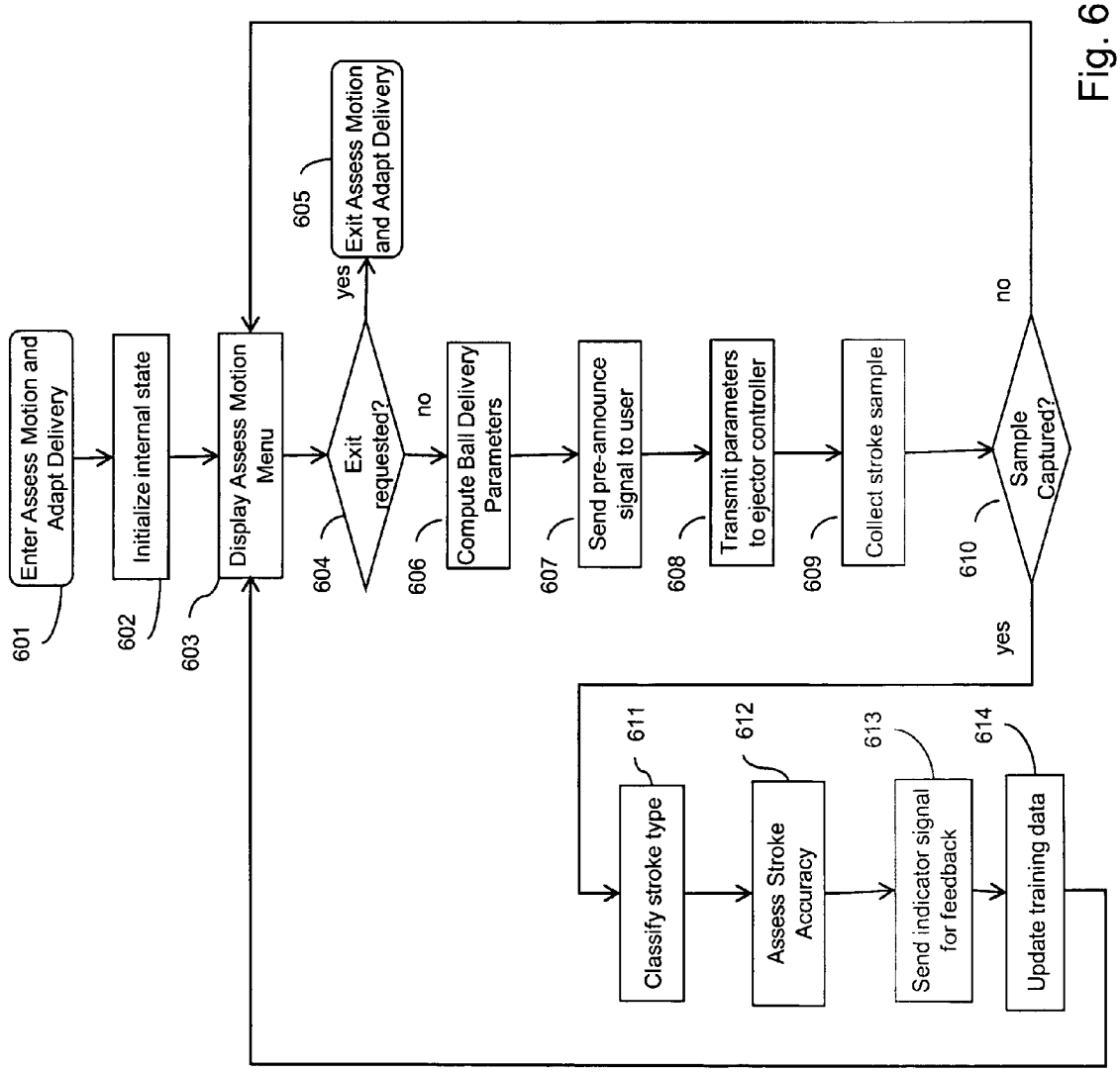
FIG. 6 details the flow chart for the Assess Motion portion of the computer program that controls the motion analysis and adaptive ball delivery.

FIG. 6 details the flow chart for the Assess Motion and Adapt Delivery portion (424) of the computer program that controls the motion analysis and feedback from FIG. 4. The program starts with Enter Assess Motion and Adapt Delivery (601). To Initialize Assess Motion (602), the present invention updates the internal state by allocating buffers for stroke data to be captured and assessed, by initializing the player performance statistics, and by initializing the weights of different ball delivery options according to any configuration options that may have been set in 419-422. Display Assess Motion Menu (603) displays the Measured Play status (814), including the last motion assessed, computed accuracy, and feedback. The user may chose to Exit Assess Motion (605) by requesting exit (604) from the Measured Play status (814). If exit is not requested, the present invention Compute Ball Delivery Parameters (606). A detailed explanation of Compute Ball Delivery parameters (606) is provided in FIG. 15. Once ball delivery parameters are computed, the shot pre-announce signal is optionally sent to the player (607), and parameters are transmitted to the ball ejector controller (608). As the ball ejector (110) executes on these updated parameters by ejecting a ball, motion sensor data is captured via Collect stroke sample (609). The procedure for Collect stroke sample (609) is explained in detail in FIG. 7.

When Collect stroke sample (609) completes, it returns an indicator of whether a complete stroke sample was received, and this indicator is tested in 610. If no sample was captured, the Assess Motion and Adapt Delivery procedure returns to Display Assess Motion Menu (603). If a sample is captured, Classify stroke type (611) computes the features detailed in FIG. 13 to create a profile of the stroke and uses the models saved to the reference database during Calibrate (413) to determine stroke type. The preferred embodiment of the present invention uses SVM in test mode to test the computed stroke profile against the models. The sample is classified as the stroke type of the model that achieves the highest accuracy classification.

The Assess Stroke Accuracy (612) uses the accuracy achieved by the model with the highest accuracy as the stroke accuracy. The stroke type determined in 611 and accuracy determined in 612 are passed to 613 for inclusion in the feedback sent to the user. The preferred embodiment of the present invention includes a rules-based method for further analyzing the motion profile to recommend specific motion adjustments. FIG. 14 provides example rules and resulting motion adjustment feedback for tennis training. Those skilled in the art will understand how similar rules-based feedback applies to other training scenarios, such as baseball and golf. After providing user feedback, Update training data (614) optionally saves the most recently collected motion profile to the reference database, if Use MP data for training is enabled. Update training data (614) also updates player performance statistics that are used to Compute Ball Delivery Parameters (606).

The feedback is displayed in the Measured Play status menu (814) and may also be communicated to the user via an audio signal. If Training Mode was enabled during Configuration, the profile for the captured stroke will be saved to the reference database. Program control then returns to Display Assess Motion Menu (603) so that the player can continue in dynamic play mode. The player may chose to look at the visual display of the Measured Play status (814), or to rely solely on the audio signal used to convey the same feedback information. Relying solely on the audio signal has the advantageous effect of allowing the player to minimize any visual distractions from their normal game play.

Figure 15:
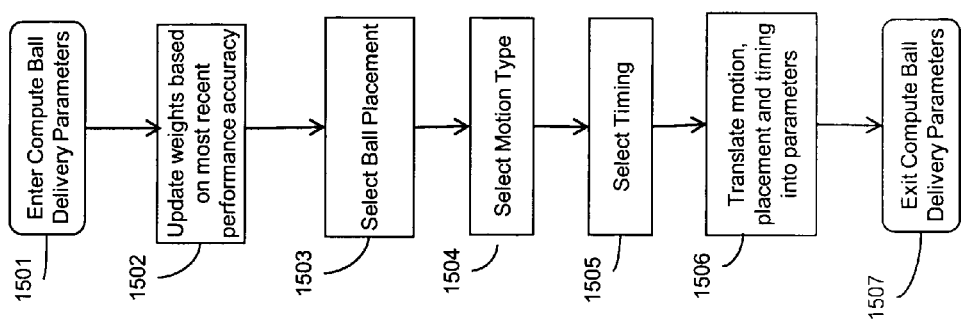
FIG. 15 the flowchart for the compute ball delivery parameters portion of the program that controls that motion analysis and adaptive ball delivery.

FIG. 15 details the flow for the Compute Ball Delivery Parameters (606) procedure. The Compute Ball Delivery Parameters procedure is entered at 1501. The preferred embodiment adapts the selection of ball placement, motion type, and timing parameters including ball speed and ball delivery inter-arrival times. FIG. 15 demonstrates an example implementation utilizing a random weighted selection technique, but those skilled in the art will understand that other control techniques can be easily applied to the present invention.

Under the random weighted select technique, each possible parameter is translated to an integer number of choices, and each choice is assigned a weight that is initialized to default values when the procedure is first entered and dynamically updated according to the most recent performance accuracy (1502). The initial values for all weights are set to 1, except options that were excluded through the manual override steps (419-422) for which weights are set to 0. The weights are updated according to an Additive Increase Multiplicative Decrease (AIMD) scheme. Specifically, if the accuracy for the most recent performance is equal to or above the average accuracy for the current training session, the weight is divided in half. If the accuracy for the most recent performance is below the average accuracy for the current training session, the weight is increased by 1. Once the weights have been set, values for each parameter are selected using random weighted selection.

Simple random weighted selection is performed by first totaling the weights of all potential choices in a given category and then selecting a random value between 0 and the total weight. The potential choices are ordered and assigned an interval proportionate to their weight. For example, if Choice-A, Choice-B, and Choice-C had weights 1, 2, 1 respectively, then the total weight would be set to 4. Additionally, if the random value, $\delta$, satisfies $0 \leq \delta < 1$, then Choice-A would be selected; if $1 \leq \delta < 3$, Choice-B would be selected; and if $3 \leq \delta < 4$, Choice-C would be selected.

After selecting the ball placement (1503), the motion type (1504), and the timing (1505) values, these values are then translated into parameters specific to the ejector controller (111) in 1506, and the Compute Ball Delivery Parameters procedure is exited (1507).

The above disclosure details how the present invention continually assesses the motions and orientations of a player during active and ongoing play scenarios, and how it adapts ball delivery and provides feedback to enable the player to improve motions and orientations based on the unbiased sensor measurements. The present invention is also well suited to design variations. For example, depending on the application of the present invention, it may be desirable for the computer program to also store stroke selection, accuracy data, and feedback data throughout the training session such that a report comprising a summary of the complete training session may be generated for retrospective analysis of the training session. In the preferred embodiment, this report is in the form of an electronic document comprising text and images. In the preferred embodiment, the user may select from a plurality of summary and detail report components. Example summary components include the average accuracy over the course of the training session or of logical subdivisions of that session. Examples of logical subdivisions for the game of tennis are match, set, and game. Additional examples of summary components include a summary of motion type selection, average accuracy for that motion type, and most common feedback for that motion type. An example of a detail report component includes a table wherein each row represents a motion analyzed and represent important features of that motion, such Time of Motion Capture, Type of Motion, Accuracy, and Feedback.

In another preferred embodiment of the present invention, it may be desirable to also attach sensors that collect game ball tracking data. The data from the game ball tracking sensors is also sent to the computer for analysis along with the sensor data collected for the user. For example, the court position at which ball-to-racket contact is made and the court position at which the ball makes court contact as a result of a stroke can be provided as a features in the stroke profile used to train and test models. The addition of external tracking sensor data enables a richer assessment and feedback, for example by incorporating the effect of the applied movements and orientations on the game ball.

While the particular dynamic motion analysis and feedback system described herein and disclosed in detail is fully capable of obtaining the goals and providing the advantageous effects herein before stated, it is to be understood that it is merely illustrative of the presently preferred embodiments of the invention and that no limitations are intended to the details of construction or design herein shown other than as described in the appended claims.

| CITATION LIST Patent Literature | | | |
| --- | --- | --- | --- |
| U.S. Pat. No. | 4,269,163 | 1981 | Feith |
| U.S. Pat. No. | 4,915,384 | 1990 | Bear |
| U.S. Pat. No. | 5,816,953 | 1998 | Cleveland |

NON-PATENT LITERATURE

[Cristianini] Nello Cristianini, John Shawe-Taylor. An Introduction to Support Vector Machines and Other Kernel-based Learning Methods. 2000. Cambridge University Press.

[Shakhnarovish] Shakhnarovish, Darrell, and Indyk. Nearest-Neighbor Methods in Learning and Vision. 2005. MIT Press.

[Safavian] Safavian, S. R.; Landgrebe, D. A survey of decision tree classifier methodology. Systems, Man and Cybernetics, IEEE Transactions. May/June 1991. Sch. of Electr. Eng., Purdue Univ., West Lafayette, Ind.

What is claimed is:

1. A ball delivery system configured to deliver ball based on an automated assessment of a player performance from a sensor data comprising:

ball ejector successively ejecting a plurality of game balls according to specified ball delivery parameters;

plurality of motion sensors, each motion sensor is configured to capture data that measures the performance of the player interacting with the ball ejecting and communicating the sensor data to a computer for analysis;

said computer is configured to (1) analyze the sensor data for the purpose of assessing performance of the player for a motion type (2) automatically select a next a recommended motion type by the computer and parameters based on the player performance assessment (3) calculate ball delivery parameters including trajectory, speed, and delay to be transmitted to the ball ejector for subsequently eject the game balls based on said player performance assessment and the recommended next motion type and parameters; (4) transmit said ball delivery parameters to a ball ejector controller to set the ball delivery parameters for subsequently ejecting the balls; and said ball ejector controller is configured to accept data signal to set the ball delivery parameters for subsequently eject the balls and adapt the ball ejector to conform to the ball delivery parameters.

2. The system in claim 1, wherein each of the said motion sensors comprises one or more of:

a tri-axis accelerometer to measure differential acceleration of the sensor;

a tri-axis gyroscope to measure differential rotation around the sensor; and a tri-axis magnetometer to measure a local magnetic field vector at each motion sensor.

3. The system in claim 1, wherein one or more of the said sensors communicate wirelessly with said computer, which also communicates wirelessly or via direct connection to ball ejector.

4. The system in claim 1, wherein the data is transmitted to a remote computer for additional processing and feedback.

5. The system in claim 1, wherein the computer and the motion sensors are integrated into a single unit that is attached to the user or the training equipment, and the computer communicates wirelessly to the ejector controller.

6. The system in claim 1, wherein: the system further comprises one or more additional sensors, which capture sensor data indicating user, or ball location; and the computer is programmed to use a location data to further analyze motion data and generate feedback signals to indicate deviations from reference performances.

7. The system in claim 1, wherein: the computer is program further programmed to produce a real-time feedback signal to indicate deviations of the measured motion from one or more reference motions and recommended motion adjustments; and the computer further comprises a mechanism to transmit an indicator of said feedback signal to the user during active play.

8. The system in claim 1, wherein the computer is programmed to produce a real-time signal to announce to the player the type of motion to be taken before the ball is delivered.

9. The system in claim 7 or claim 8, wherein the indicator signal for feedback comprises one or more of: an audio signal, a visual signal, and a physical signal.

10. The system in claim 1, wherein the computer program further comprises a mechanism to analyze captured sensor data and to produce a report with a user-specified or default set of summary and detail information on motions, accuracy, and feedback over an entire training session.

* * * * *